US 9,924,862 B2

(12) United States Patent
Brown et al.

(10) Patent No.: US 9,924,862 B2
(45) Date of Patent: Mar. 27, 2018

(54) OPHTHALMOSCOPE

(71) Applicant: Optos PLC, Dunfermline (GB)

(72) Inventors: William Brown, Durham, NC (US); Michael E. Sullivan, Durham, NC (US); Anthony Corcoran, Dunfermline (GB); Derek Swan, Dunfermline (GB)

(73) Assignee: Optos PLC, Dunfermline (GB)

( * ) Notice: Subject to any disclaimer, the term of this patent is extended or adjusted under 35 U.S.C. 154(b) by 0 days.

(21) Appl. No.: 14/422,671

(22) PCT Filed: Oct. 1, 2013

(86) PCT No.: PCT/GB2013/052556
§ 371 (c)(1),
(2) Date: Feb. 19, 2015

(87) PCT Pub. No.: WO2014/053824
PCT Pub. Date: Apr. 10, 2014

(65) Prior Publication Data
US 2015/0216408 A1 Aug. 6, 2015

(30) Foreign Application Priority Data
Oct. 1, 2012 (GB) .................................. 1217538.6

(51) Int. Cl.
*A61B 3/14* (2006.01)
*A61B 3/00* (2006.01)
(Continued)

(52) U.S. Cl.
CPC ............ *A61B 3/102* (2013.01); *A61B 3/1015* (2013.01); *A61B 3/1025* (2013.01); *A61B 3/1225* (2013.01); *A61B 3/14* (2013.01)

(58) Field of Classification Search
CPC ......... A61B 3/103; A61B 3/14; A61B 3/1225; A61B 3/113; A61B 3/1015
(Continued)

(56) References Cited

U.S. PATENT DOCUMENTS 5,815,242 A  9/1998 Anderson et al.
5,975,697 A  11/1999 Podoleanu et al.
(Continued)

FOREIGN PATENT DOCUMENTS

CN  101489468 A  7/2009
CN  101884524     11/2010
(Continued)

OTHER PUBLICATIONS

Gärtner, Andreas, "International Search Report," prepared for PCT/GB2013/052556, dated Feb. 18, 2014, six pages.
(Continued)

*Primary Examiner* — Dawayne A Pinkney
(74) *Attorney, Agent, or Firm* — Foley & Lardner LLP; Pavan Agarwal; Shabbi S. Khan

(57) ABSTRACT

A scanning laser ophthalmoscope (SLO) for imaging the retina of an eye comprises a source (12) of collimated light, a scanning device (14, 16, 1328, 1319), a scan transfer device (20) and a detector (1310). The scan transfer device has a first focus (16) at which an apparent point source is provided and a second focus (24) at which an eye (524, 1324) may be accommodated. The scan transfer device transfers a two-dimensional collimated light scan from the apparent point source into the eye. An optical coherence tomography (OCT) system (900) is combined with the SLO, the OCT system providing OCT reference and sample beams. The OCT sample beam (902) propagates along the same optical path as of the SLO collimated light through the scan transfer device. An aberration compensator (1204, (Continued)

1316) automatically compensates for systematic aberrations and/or changes in wavefront introduced by scanning elements and the scan transfer device as a function of scan angle.

34 Claims, 6 Drawing Sheets

(51) Int. Cl.
*A61B 3/10* (2006.01)
*A61B 3/12* (2006.01)

(58) Field of Classification Search
USPC ............... 351/200, 206, 221, 205, 210, 246
See application file for complete search history.

(56) References Cited

U.S. PATENT DOCUMENTS

| 2007/0046948 | A1 | 3/2007 | Podoleanu et al. |
| 2010/0141895 | A1* | 6/2010 | Cairns ................. A61B 3/1225 |
| | | | 351/206 |
| 2010/0328606 | A1 | 12/2010 | Peyman |
| 2011/0234978 | A1* | 9/2011 | Hammer ................ A61B 3/102 |
| | | | 351/208 |
| 2013/0169971 | A1 | 7/2013 | Brown et al. |

FOREIGN PATENT DOCUMENTS

| CN | 102038487 | 5/2011 |
| CN | 102525403 | 7/2012 |
| EP | 2 382 914 | 11/2011 |
| EP | 2465413 A1 | 6/2012 |
| GB | 2440163 A | 1/2008 |
| JP | S-6420827 | 1/1989 |
| JP | H-10267830 | 9/1998 |
| JP | 2012-020061 | 2/2012 |
| WO | WO-2010/125394 A1 | 11/2010 |
| WO | WO-2011121962 A1 | 10/2011 |
| WO | WO-2011135348 A2 | 11/2011 |

OTHER PUBLICATIONS

Chinese Examination Report Application No. 201300476859 dated Jan. 21, 2016 and Summary of Chinese Examination Report (English Translation), 16 pages.
Search Report for CN201380047685.9 dated Jan. 11, 2016.
Murjat et al., "High resolution, multimodal clinical ophthalmic imaging system", published 2002, Opt Express 18(11), pp. 11607-11621.
Search Report for GB 1217538.6 dated Jun. 27, 2013.
Zawadzki et al., "Integrated adaptive optics optical coherence tomography and adaptive optics scanning laser ophthalmoscope system for simultaneous cellular resolution in vivo retinal imaging", published 2011, Biomed Opt Express 2(6), pp. 1674-1686.
Japanese Office Action Application No. 2015-533702 dated May 16, 2017, 7 pages. (with English translation).

* cited by examiner

OPHTHALMOSCOPE

PARTIES TO A JOINT RESEARCH AGREEMENT

At least some of the subject matter described in this application is a result of activities undertaken within the scope of a joint research agreement between Optos, PLC and Wasatch Photonics Inc. that was in effect on or before the date of the research leading to this application was made.

The present invention relates to improvements in or relating to scanning laser ophthalmoscopes (SLOs), and in particular to the introduction of wide field structural retinal imaging capabilities to scanning laser ophthalmoscopes.

It is well known to image the retinal structure of a subject using Optical Coherence Tomography (OCT). OCT is an interferometric technique whereby an illumination source is directed towards the retina of a subject and the reflected beam, or sample arm, is combined with light in a controlled reference arm and whereby the interference properties of the combined beam are used to determine and display the structure of the imaged retina.

It is also well known to image the retina of a subject using a Scanning Laser Ophthalmoscope (SLO) to obtain an image of the retina at multiple wavelengths, where specific wavelengths represent specific layers of the retina.

In recent times, wide field SLOs have become available. In these devices, the light from an illuminator is scanned in a raster fashion and transferred by one of more optical elements to produce a one-dimensional collimated light scan on the subject retina.

One embodiment of a wide-field SLO uses optical elements that comprise two foci (for example an ellipsoidal mirror) to produce a one-dimensional collimated light scan on the retina such that the scanned illumination appears as an apparent scanning light source at the pupil of the eye.

An alternative embodiment of a wide-field SLO may use refractive optical elements to generate a wide-angle field of view about the subject pupil or extend the field of view of a conventional SLO.

It is known to provide a standard narrow field SLO with an integrated OCT system. The simultaneous measurement of the confocal fundus image via the SLO optics and the tomographic image via the OCT optics provides efficiencies of operation and means that more information can be gathered from a single procedure.

However, successful incorporation of an OCT imaging system within a wide field imaging system or wide-field SLO has not been achieved. This is because the optical aberrations and phase effects in the optical system and variance in the physiological and optical properties of the subject eye incurred in a wide-field system compromise the efficacy of the sample beam collection and recombination with the reference beam, disrupting the interferometric data set and, hence, the structural information of the subject retina. As a result, the data integrity and image quality required to support the diagnostic utility of this modality is compromised.

There is a need for improvements to enable a practical way of integrating an OCT system within a wide-field SLO so that the structural information relating to any part of the subject retina can be obtained to supplement and support information from the wide-field fundus image.

According to a first aspect of the disclosure there is provided a scanning ophthalmoscope for scanning the retina of an eye comprising: a source of collimated light and a scanning device which together provide a two-dimensional collimated light scan from an apparent point source; and a scan transfer device comprising a first focus at which the apparent point source is provided and a second focus at which an eye may be accommodated, such that the scan transfer device transfers the two-dimensional collimated light scan from the apparent point source into the eye; an optical coherence tomography (OCT) system comprising a radiation source and an optical system that together provide OCT reference and sample beams where the sample beam propagates along an optical path that is at least in part the same as an optical path of the light emitted by the SLO collimated light source and propagating through the scan transfer device, and an aberration compensator that ensures integrity of the OCT reference beam and sample beam.

By "ensuring integrity" of the OCT reference beam and sample beam it is meant that the conditions required for optimum retinal sampling and successful recombination of the sample and reference beams are maintained. In particular embodiments, the aberration compensator (which may be a combination of elements) functions to compensate for aberrations and changes in wavefront introduced by the scan elements and scan transfer device as a function of scan angle.

It is noted that the use of adaptive optics in retinal imaging applications has been proposed previously, for example in: Mujat et al in "High resolution multimodal clinical ophthalmic imaging system", Optics Express 2010 May 24| 18(11)| 11607-11621. However, the adaptive optics in these known examples is designed only to detect and correct ocular aberrations, that is aberrations caused within the subject's eye. It does not address the problem of aberrations or changes in wavefront introduced by elements of the optical system in an automated, cost-effective manner. These aberrations which are fixed and systematic as a function of scan angle prevent both effective sampling and subsequent collection of the OCT signal. By providing the novel aberration compensator, the invention enables automated, high resolution OCT to be combined with wide-field SLO in a manner not enabled with prior designs. Also, conventional adaptive optics methods in SLO and OCT rely on a Hartmann Shack wavefront sensor arrangement, or similar, to detect and correct for aberrations in closed loop control. This is expensive and un-necessary for implementation of the present invention, for which correction of systematic aberrations synchronously with scanning operations can be designed and built in.

Optionally, the aberration compensator comprises a wavefront coding means for altering the wavefront of the illumination emitted by the OCT illumination source, to compensate for aberrations and changes in wavefront introduced by the scan elements and scan transfer device as a function of scan angle.

Optionally, the wavefront coding means comprises a device for altering the spatial properties of the incident beam and/or the form of the incident beam wavefront such that the spatial extent of the input OCT signal on a retinal surface is minimised after propagation through the scan relay and scan transfer means.

Optionally, the wavefront coding means comprises a variable magnification stage to optimise the beam diameter at any point in a scan field.

Optionally, the wavefront coding means comprises a variable focus element.

Optionally, the wavefront coding means comprises at least one from the group comprising: a liquid lens, an adaptive lens, a spatial light modulator, a variable position lens or lens system, adaptive optical system.

Optionally, the aberration compensator comprises a means for altering the optical path length of the OCT reference arm, such that the sample and reference path lengths remain matched throughout said scanning, for example over the full extent of a retinal scan.

Optionally, the means for altering the optical path length of the OCT reference arm comprises a motorised linear translation stage whereby the optical path length may be increased or decreased to match the sample arm path length throughout said scanning.

Optionally, the means for altering the optical path length of the OCT reference arm comprises a series of rotating optical elements to provide adjustable path length control such that the optical path length may be increased or decreased to match the sample arm path length throughout said scanning.

Optionally, the means for altering the optical path length of the OCT reference arm comprises a series of fixed paths of varying path length that may be selectively enabled to match the input sample path length.

Optionally, the means for altering the optical path length of the OCT reference arm comprises a feedback mechanism so that the path length can be automatically altered during a scan to compensate for path length variance across the scanned object.

Optionally, the means for altering the optical path length of the OCT reference arm comprises means for automatically altering the path length in discrete steps between each sample during a scan.

Optionally, the aberration compensator comprises a variable phase retardation stage such that the polarisation state of the signal and reference beams remains matched throughout said scanning.

Optionally, the phase retardation stage is provided in the OCT reference arm.

Optionally, the phase retardation stage comprises one of: a waveplate; a series of waveplates; a soleil-babinet type compensator; a stress-induced birefringence controller.

It is also to be appreciated that the provision of two foci by the scan transfer device as described above can be accomplished for systems based either on reflective optical elements (for example ellipsoidal mirrors) or refractive optical elements (for example a lens system). Indeed, the scan transfer device may also comprise a hybrid system having a mixture of reflective and refractive optical elements.

Optionally, the scan transfer device comprises an aspherical mirror, an ellipsoidal mirror, a pair of parabola mirrors or a pair of paraboloidal mirrors. An ellipsoidal mirror, for example, allows ultra wide-field scanning, but introduces aberrations at extreme scan angles that would defeat the acquisition of OCT images from peripheral regions of the retina.

Optionally, the scanning ophthalmoscope further comprises a scan relay device and wherein the source of collimated light, the scanning device and the scan relay device combine to provide the two-dimensional collimated light scan from the apparent point source.

Optionally, the scan relay device comprises two foci and one focus of the scan relay device is coincident with one focus of the scan transfer device.

Optionally, the scan relay device comprises an elliptical mirror, an aspherical mirror, and ellipsoidal mirror, a pair of parabola mirrors or a pair of paraboloidal mirrors.

Optionally, the scan transfer device comprises one or more refractive optical elements, wherein a scan angle of the scanning device is changed by the refractive optical element(s) and an eye of a subject may be accommodated at a focal point of the refractive optical element(s).

Optionally, the one or more refractive optical elements comprise a lens or a system of lenses.

Optionally, the scanning device comprises a first scanning element and a second scanning element.

Optionally, the rotational axis of the second scanning element is substantially parallel or perpendicular to a line joining the two foci of the scan transfer device.

Optionally, the rotational axis of the first scanning element is substantially parallel or perpendicular to a line joining the two foci of the scan transfer device.

Optionally, in the provision of the two-dimensional collimated light scan from the apparent point source, the scan relay device produces a vertical scan component, and the line joining the two foci of the scan transfer device either lies substantially on a plane defined by the vertical scan component produced by the scan relay device or perpendicular to the plane defined by the vertical scan component produced by the scan relay device.

Optionally, the scanning ophthalmoscope further comprises a light detection device for detecting light reflected from the retina to produce an image of the scanned area of the retina.

Optionally, the OCT radiation source is provided at a position along the optical path before the first scanning element.

Optionally, the OCT radiation source is provided at a position along the optical path after the first scanning element and before the second scanning element.

Optionally, the OCT radiation source is provided via a separate input path and directed to a retina via the scan transfer means at an arbitrary angle relative to the SLO beam.

According to a second aspect of the disclosure there is provided a method of scanning the retina of an eye comprising the steps of: providing a source of collimated light and a scanning device which together provide a two-dimensional collimated light scan from an apparent point source; providing a scan transfer device comprising a first focus at which the apparent point source is provided and a second focus at which an eye may be accommodated, and wherein the scan transfer device transfers the two-dimensional collimated light scan from the apparent point source into the eye; providing an optical coherence tomography (OCT) system comprising a radiation source and an optical system that together provide OCT reference and sample beams where the sample beam propagates along at least part of the same optical path of the light emitted by the SLO collimated light source and propagating through the scan transfer device, and compensating for aberrations to ensure integrity of the OCT reference beam and sample beam.

Optionally, the step of compensating for aberrations comprises altering the wavefront of the illumination emitted by the OCT illumination source, to compensate for aberrations and changes in magnification introduced by the scan elements and scan transfer device as a function of scan angle.

Optionally, the step of compensating for aberrations comprises altering the optical path length of the OCT reference arm, such that the sample and reference path lengths remain matched over the full extent of a retinal scan.

Optionally, the step of compensating for aberrations comprises controlling the phase of OCT illumination such that the polarisation state of the signal and reference beams remains matched over the full extent of a scan.

Each of the various features of the first aspect mentioned above may also give rise to corresponding aspects of a method according to the disclosure, including for example and without limitation the steps of providing and/or using the various apparatus mentioned.

BRIEF DESCRIPTION OF THE DRAWINGS

Embodiments of the invention will now be described, by way of example only, with reference to the accompanying drawings, in which.

DETAILED DESCRIPTION OF EXEMPLARY EMBODIMENTS

Figure 1:
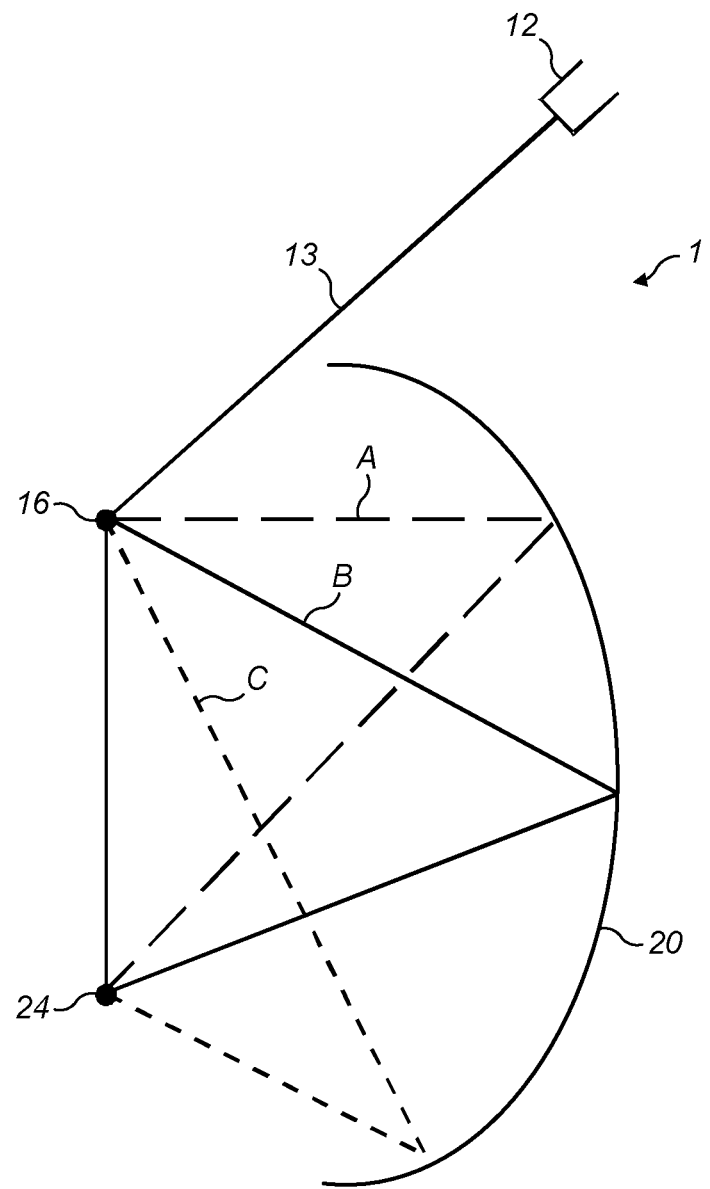
FIG. 1 is an optical schematic showing a scanning laser ophthalmoscope (SLO) according to the disclosure provided with a scan transfer device for transferring a two-dimensional collimated light scan into an eye of a subject.

FIG. 1 shows an implementation of a wide field scanning laser ophthalmoscope (SLO) 1 including a source of collimated light 12, a scanning device comprising a scanning element 16, and a scan transfer device 20. The source of collimated light 12 is directed towards the patient via the scanning device and scan transfer means such that an ultra-wide field scan angle is achieved at the subject pupil plane 24. In the present disclosure, "widefield" scanning refers to a scan angle in excess of 50 degrees in one or two dimensions, while "ultra-wide field" is used to refer to a scan covering substantially the entire retina. This collimated light source may be a laser for SLO applications or, in the case of OCT, may be a superluminescent diode (SLD).

However, it should be appreciated that any suitable source of collimated light could be used, such as a single frequency laser diode, vertical-cavity surface-emitting laser, or other source that has enough intensity and to be well collimated and produce adequate retinal illumination. In OCT applications, an SLD may be used due the short coherence lengths required to discriminate the retinal layers from the resultant interferometric data. The SLD may be free space or fibre coupled into standard or polarisation maintaining fibre to the scan system.

The scanning element 16 may be an oscillating plane mirror, such as a galvanometer mirror. Alternatively the scanning element 16 may be a MEMS mirror. Alternatively the scanning element 16 may be a rotating mirror, prism or polygon scanner. Alternatively, the scanning element 16 may be a resonant mirror. The scanning element 16 creates a two-dimensional collimated light scan of the laser beam 13.

Figure 2:
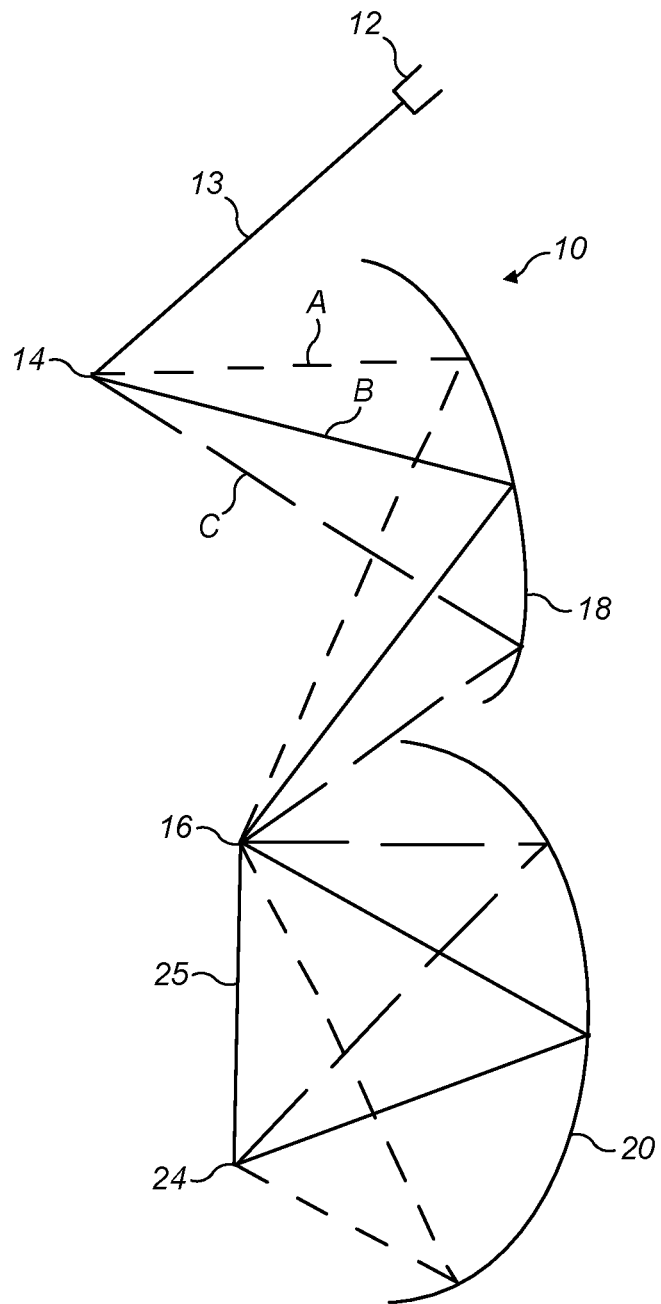
FIG. 2 is an optical schematic showing an SLO according to an alternative embodiment of the disclosure comprising first and second scanning elements, a scan relay device and a scan transfer device.

With reference to FIG. 2, another implementation of a wide field scanning laser ophthalmoscope (SLO) 10 includes a source of collimated light 12, a scanning device, scan relay device 18 and scan transfer device 20. The scanning device comprises a first scanning element 14 and a second scanning element 16.

In the embodiment described here the source of collimated light 12 is directed towards the patient via the scanning elements, scan relay and scan transfer means such that an ultra-wide field scan angle is achieved at the subject pupil plane 24. This collimated light source may be a laser for SLO applications or, in the case of OCT, may be a superluminescent diode. However, it should be appreciated that any suitable source of collimated light could be used, such as a single frequency laser diode, vertical-cavity surface-emitting laser, wavelength swept laser source, pulsed laser source, or other source that has enough intensity and to be well collimated and produce adequate retinal illumination. In OCT applications, an SLD may be used due the short coherence lengths required to discriminate the retinal layers from the resultant interferometric data. The SLD may be free space or fibre coupled into standard or polarisation maintaining fibre to the scan system. A swept source laser may also be used in OCT applications, whereby the wavelength of the source is tuned over a given range.

The first scanning element 14 may be an oscillating plane mirror, such as a galvanometer mirror. Alternatively the first scanning element may be a MEMS mirror. Alternatively the first scanning mirror may be a rotating mirror, prism or polygon scanner. Alternatively, the first scanning mirror may be a resonant mirror. Alternatively, the first scanning element may be a single element or arrangement of two elements as described to provide a two dimensional scan at point 14, providing a two dimensional scan pattern over the scan relay 18. In this arrangement, the first scanning element provides either a vertical, horizontal or patterned two dimensional scan to a point on the second scan element via the scan relay.

The second scanning element 16 may be an oscillating plane mirror, such as a galvanometer mirror. Alternatively the second scanning element may be a MEMS mirror. Alternatively the second scanning mirror may be a rotating mirror, prism or polygon scanner. Alternatively, the second scanning mirror may be a resonant mirror. The first scanning mirror 14 and the second scanning mirror 16 axes are arranged to create a two-dimensional collimated light scan, in the form of a raster scan pattern of the laser beam 13. The alignment of the first and second scanning mirrors may be orthogonal, substantially orthogonal or arranged to generate an arbitrary scan geometry about the scan relay and scan transfer means.

The second scanner 16 provides a plurality of second one or two-dimensional collimated light scans, which, in this embodiment of the invention, comprises horizontal one-dimensional scans, vertical one dimensional scans or arbitrary two dimensional patterns of the laser beam 13.

FIG. 2 illustrates the path of the laser beam 13 in a one-dimensional scan produced by one oscillation of the first scanning mirror 14. Path A is an example of the laser beam reflected from the galvanometer mirror 14 at the start of the rotation; path B is an example of the laser beam reflected from the first scanning mirror 14 at an intermediate point of the rotation; and path C is an example of the laser beam reflected from the first scanning mirror 14 at the end of the rotation.

The first scanning mirror 14 and the second scanning mirror 16 thus together create a two-dimensional collimated light scan in the form of a raster scan pattern from a single point in space 24.

The first and second scanning mirrors 14, 16 have operating parameters which include the amplitude of the oscillation and the rotational offset of the oscillation. The operating parameters also include the velocity of oscillation. Both of these operating parameters may be selected to control the direction and pattern of the two-dimensional collimated light scan from the apparent point source.

The first and second scanners 14, 16 may be housed in a rotation mount (not shown) that can adjust the centring (or eccentricity) of the scanned laser beam 13 on the retina, which provides the ability to "move" the imaging field across the retina.

The scan relay device 18 has two foci. In the embodiment described here the scan relay device 18 is an ellipsoidal mirror, and is referred to as a slit mirror. It should be appreciated, however, that the scan relay device 18 may have an alternative form.

The first scanning mirror 14 is positioned at a first focus of the scan relay device 18 and the resonant scanner 16 is positioned at the second focus of the scan relay device 18.

The scan transfer device 20 may be an aspherical mirror in the form of an ellipsoidal mirror, and may be referred to as a main mirror. The main mirror 20 has two foci. In the embodiment described and illustrated here, the main mirror 20 is configured to provide a 200 degree field of view (external angle) in both the vertical and horizontal directions (i.e. 200 degree×200 degree) on the retina. However, it should be appreciated that the main mirror scan transfer device may be configured to provide an substantially lesser or substantially greater field of view in both horizontal and vertical directions.

The second scanner 16 is also positioned at a first focus of the main mirror 20. A subject's eye 24 is positioned at a second focus of the main mirror 20.

The laser beam 13 is thus conveyed to the subject's eye 24, via the first and second scanning elements, 14, 16, the slit mirror 18, and the main mirror 20.

The scanning ophthalmoscope may be able to produce such scans of the retina of the eye, through a 2 mm undilated pupil of the eye. However, it should be appreciated that the SLO is also capable of producing scans of the retina of the eye through, for example, an 8 mm dilated pupil.

The components of the SLO 10 are arranged such that the apparent point source is stationary at the pupil of the eye. This ensures that a beam of reflected light from the retina of the subject's eye 24 is conveyed back through the optical path of the SLO 10. The reflected light is used to produce an image of the subject's retina in a known manner or, in the case of OCT, provide the sample arm illumination back to the OCT interferometer.

Judicious matching of eccentricities of the slit mirror 18 and the main mirror 20 provides well behaved deviation from perfect scan linearity. Symmetric deviation, as a function of angle from the optic axis of the eye, enables simple compensation of distance measurements on the retina in software, and an adequately intuitive retinal display representation.

The components of the SLO 10 may be arranged such that the rotational axis of the first scanner 16 is substantially parallel to a line 25 joining the two foci of the main mirror 20, such that the laser beam 13 is scanned across the secondary axis of the slit mirror 18. Furthermore, in the provision of the two-dimensional collimated light scan from the apparent point source, the first scanning mirror 14 produces a one-dimensional or two-dimensional scan which is incident on the slit mirror 18. The slit mirror 18 also therefore produces a one-dimensional or two-dimensional scan. The components of the SLO 10 are arranged such that the line 25 joining the two foci of the main mirror 20 lies substantially on a plane defined by the one-dimensional vertical scan produced by the slit mirror 18. This arrangement of components offers a number of advantages.

It is known to capture retinal images using optical coherence tomography (OCT). This is an interferometric technique wherein radiation from an illumination source is split into a reference beam and a sample beam. The sample beam is directed towards a sample to be imaged and then the reflected (or transmitted) light is then recombined with the reference beam. The resulting interference pattern forms the basis on which an image of the underlying structure can be formed.

OCT is typically used with near-infrared (NIR) radiation, which allows imaging below the surface in biological tissue, which is relatively deep compared with the depth of imaging that can be achieved with other non-contact techniques such as confocal microscopy for example.

Figure 3:
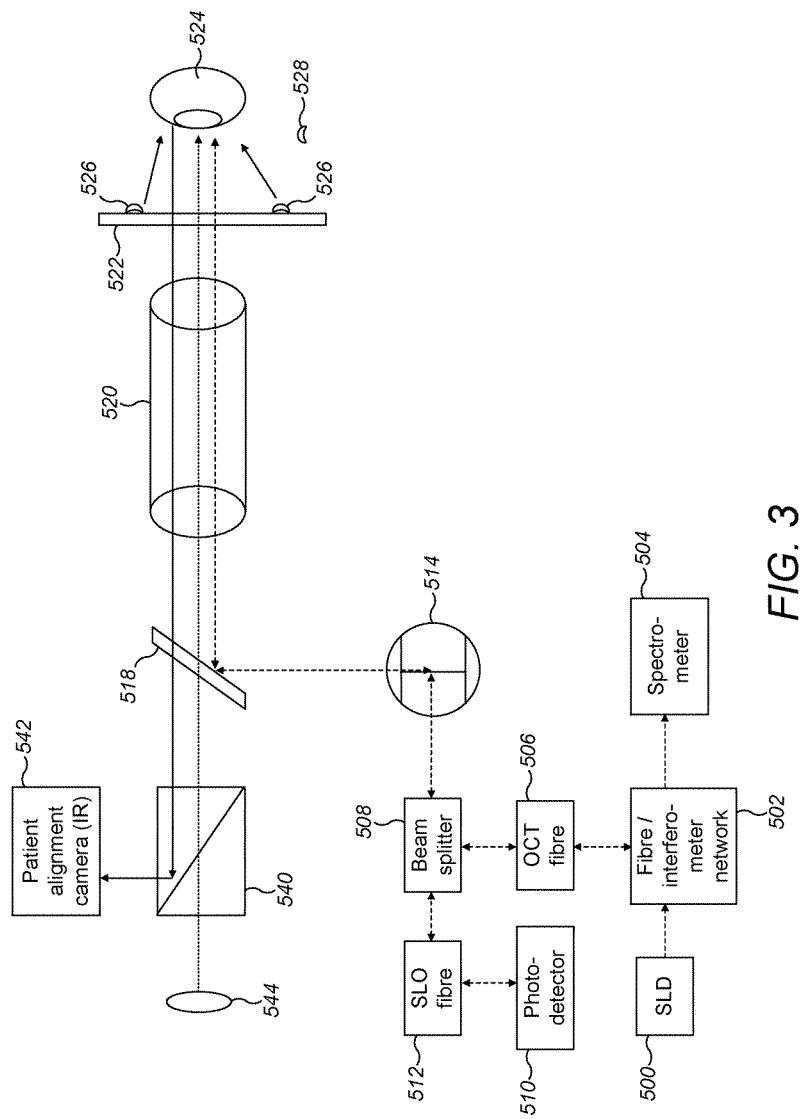
FIG. 3 illustrates a narrow field combined SLO and optical coherence tomography OCT system.

A schematic diagram of a combined narrow field scanning laser ophthalmoscope and optical coherence tomography instrument is shown in FIG. 3. Here, an OCT optical system is provided which injects OCT beams into the light path of the SLO.

A light source 500 such as a Super Luminescent Diode (SLD) is directed to a fibre/interferometer network 502 which provides and output to OCT fibre 506 and spectrometer 504. The OCT fibre 506 directs light to a local OCT scanner 514 which may for example be a galvanometer including scanning X and Y mirrors.

The scanning element 514 directs the illumination towards hot mirror 518 and onwards through a scan relay 520 such as a lens box and onwards to a patient's eye 524 via patient alignment module 522. This module 5222 provides a patient fixation target via projection of an optical signal which may for example comprise visible LEDs 526 and fixation LED 528.

A localised SLO may be derived using the return signal from the OCT illumination via beam splitter 508, which directs the return illumination into a local SLO fibre 512 and to photodetector 510, which can be used to generate a detailed SLO image in combination with the OCT acquisition.

The system of FIG. 3 also comprises beam splitter 540, patient alignment camera 542 and light source 544 which may be an organic LED or suitable alternative.

The combination of an SLO image with an OCT image provides a comprehensive diagnostic capability, combining reflective fundus imaging and structural imaging of the retina. The scanning laser ophthalmoscope may provide high resolution images and retinal tracking before, during and after the OCT scan; and may track the location of a circular OCT imaging area around the optic disc and ensure that the OCT scan is accurately positioned. The SLO can then ensure that the scan is obtained from the same location during follow up examinations of a patient for measurements of change to their retina.

Both the SLO confocal fundus image and the OCT image may be generated through the same optics and may be pixel-to-pixel correspondent which ensures precise OCT registration and orientation.

A wide field SLO system comprises scan relay and scan transfer devices which may for example be ellipsoidal mirrors. These devices introduce aberrations which prevent the integration of an OCT capability due to the precise matching of various parameters that must be maintained between the reference and sample beams in order to obtain an image. Specifically, the change in radius of curvature of the mirror optics as a function of scan angle results in a change in the focal properties of the beam incident onto the retina, compromising the transverse and axial resolution which significantly impairs the ability to resolve retinal structural detail. In addition, this change in local radius of curvature also compromises the ability to re-couple the return OCT light effectively into the OCT engine such that it can couple with the reference arm to produce the required interference fringes. In addition, the wide angle scanning results in a change in input and return polarisation, which must be compensated for in order to effectively re-couple the sample and reference arms. In addition, wide field scanning also introduces significant changes in the optical path length in the sample arm. If this is not corrected, the range, and hence field of view, will be significantly limited and wide field imaging will not be possible.

The present invention provides for the incorporation of an OCT imaging apparatus within a wide field scanning laser ophthalmoscope system. This is achieved through the incorporation of correction mechanisms designed to compensate for optical aberrations of the scan relay device and scan transfer device which form part of the wide field imaging system and to compensate for optical path length variance of the sample arm over the complete wide field scan.

In the arrangement shown in FIG. 2 for example, aberrations are introduced to the collimated source as the source is scanned through the major axis of the elliptical sections of the scan relay device and scan transfer device. This aberration is predominantly first order focal aberration and astigmatism. In general, the use of any non-spherical reflective elements or wide field transmission systems shall necessarily introduce aberrations to the scanning beam.

An OCT scan engine may comprise an illumination source and vertical and horizontal scan means such that the scan engine can provide a two-dimensional scanning OCT source.

Alternatively, a directed one dimensional scanning OCT source may be provided.

The apparatus may be configured such that the apparent point of source of the OCT sub system is co-located with the SLO source at the second scanning element.

Figure 5:
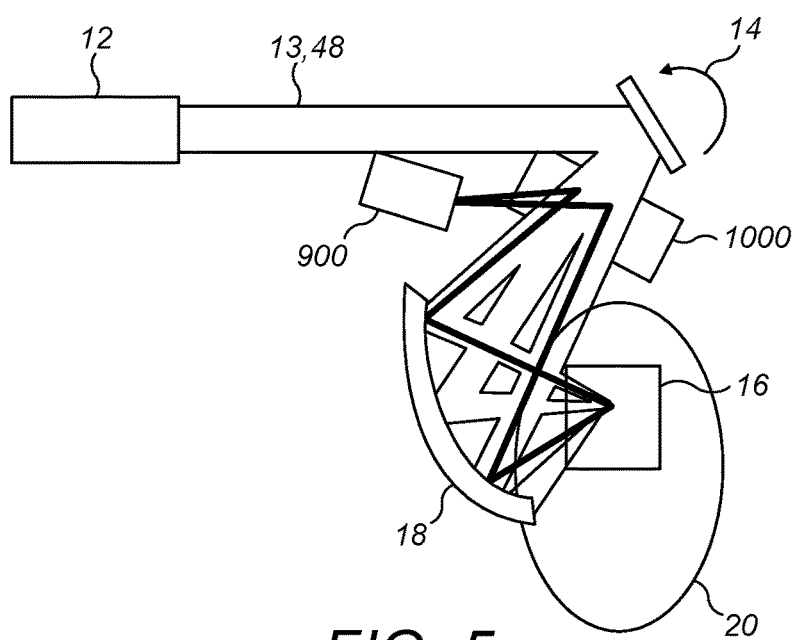
FIG. 5 illustrates an embodiment of a combined SLO and OCT wide field imaging system, wherein the OCT and SLO illumination sources are combined after a first scanning element but prior to a scan compensator and second scanning element along an optical path.
Figure 6:
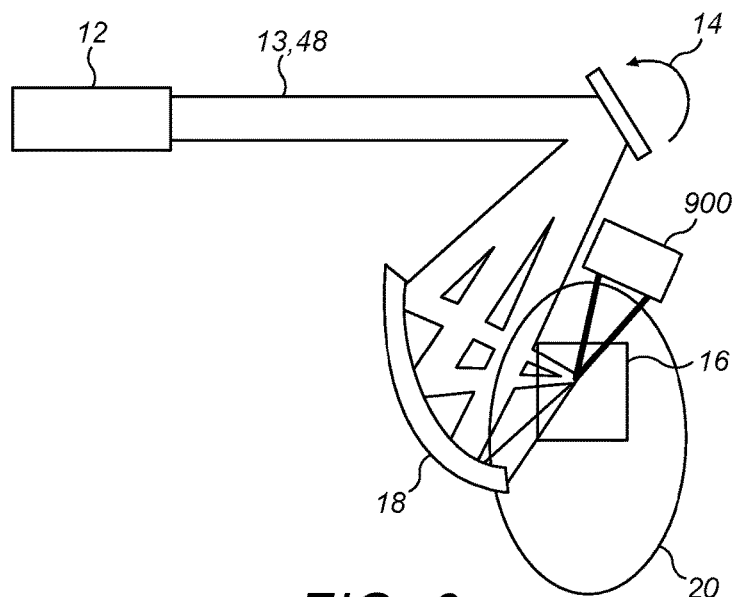
FIG. 6 illustrates an embodiment of a combined SLO and OCT wide field imaging system in which the OCT source is provided via a separate input path from the SLO source.

The OCT imaging system may be provided in various different configurations. Examples of some of the options are illustrated in FIGS. 4, 5 & 6, which show the OCT imaging system incorporated with an SLO system of the type shown in FIG. 2.

Figure 4:
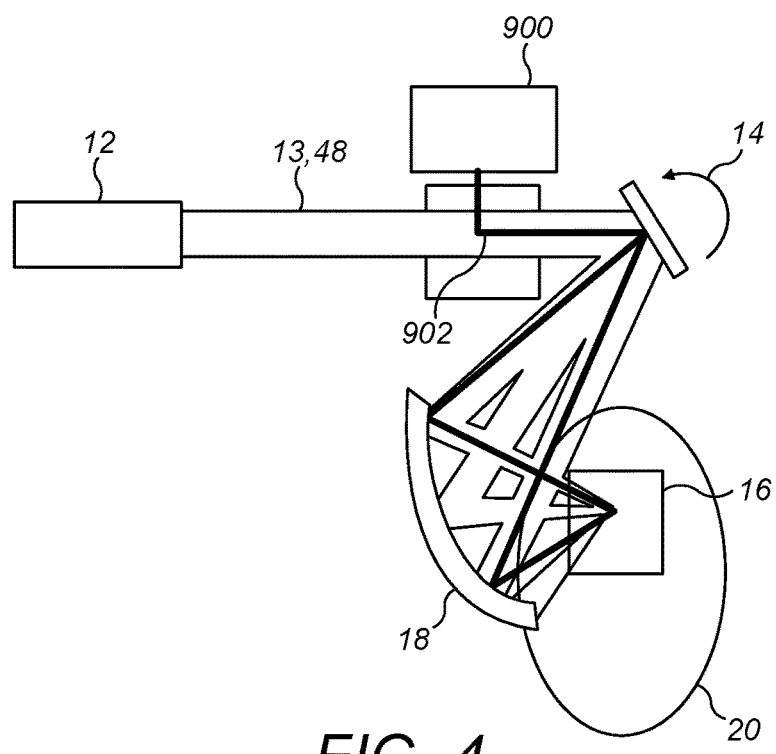
FIG. 4 illustrates an embodiment of a combined SLO and OCT wide field imaging system, in which the OCT and SLO sources are combined before a first scanning element in an optical path.

FIG. 4 illustrates a first example configuration wherein the OCT and SLO beams are combined before the first scanning element 14. In this arrangement, the SLO illumination source 12, first scanning element 14, second scanning element 16, scan relay device 18 and scan transfer device 20 are provided as before. The illuminator 12 may emit a laser beam 13. In addition, OCT optics 900 are provided. The OCT optics 900 provide a collimated beam from a fiber delivered OCT source via the OCT interferometer such that the emitted beam 902 forms the OCT sample beam. The OCT optics may also contain local scanning optics such that an OCT scan point can be relayed through the scan relay and scan transfer means to the patient retina.

The illumination source used for the OCT optics 900 may in one example comprise a super luminescent diode (SLD) which may for example operate over any region of the NIR-IR spectrum. Alternatively, the illumination source used for the OCT optics 900 may be a swept laser source or a pulsed laser source.

In this configuration the 2D OCT scan system is propagated to the scan relay device 18 and scan transfer device 20 via the first scan element 14.

The optical system in the OCT scan system propagates the OCT illumination such that the apparent point source is co-located at the first scan element 14. The OCT illumination can then be directed to the entirety of the retina which is addressable by the combination of scanning elements 14, 16, or a sub-section of the retina by fixed angle settings of the scanning elements 14, 16.

Moreover, the subsection of the addressed retina can then be imaged via the integrated scan means in the 2D OCT scan system, thereby providing utility for wide field 2D and 3D images or targeted 2D or 3D subsections of the retina.

FIG. 5 illustrates a second example configuration where the OCT and SLO beams are combined after the first scanning element 14 but before the second scanning element 16. In this configuration, the OCT illumination is directed to the second scanning element 16 via the scan relay device 18 and an additional optical element 1000 which may for example be a beam splitter.

The optical layout is such that the apparent point source is located at the second scanning element 16, corresponding to one focus of the scan transfer device 20. The OCT illumination can then be directed to the entirety of the retina addressable by the rotation of scanning element 16, rotation of an optical element within the OCT optics 900 or by rotation of the OCT optical assembly. In addition, the OCT illumination can be directed to a sub-section of the retina by fixed angle settings of the second scanning element 16 and integrated OCT scan system within the OCT optics 900.

Moreover, the subsection of the addressed retina can then be imaged via the integrated scan means in the 2D OCT scan system, thereby providing utility for wide field retinal 2D and 3D images or targeted 2D or 3D subsections of the retina.

FIG. 6 illustrates a third example configuration in which the OCT and SLO beams are combined directly on the scanning element. In this configuration, the SLO and OCT images do not have to be on the same point on the retina. The OCT illumination is directly coupled to the second scanning element 16 such that the apparent point source is located at the second scanning element 16, corresponding to one focus of the scan transfer device 20. This path is independent of the scan relay device 18 or first scanning element 14.

The OCT illumination can then be directed to the entirety of the retina addressable by the rotation of scanning element 16, rotation of an optical element within the OCT optics 900 or by rotation of the OCT optical assembly. In addition, the OCT illumination can be directed to a sub-section of the retina by fixed angle settings of the second scanning element 16 and integrated OCT scan system within the OCT optics 900.

Moreover, the subsection of the addressed retina can then be imaged via the integrated scan means in the 2D OCT scan system, thereby providing utility for wide field retinal 2D and 3D images or targeted 2D or 3D subsections of the retina.

In each of the above configurations the OCT illumination may be scanned across or directed to a portion of the elliptical section of either or both the scan relay device 18 or scan transfer device 20. In other words, the OCT illumination must be reflected from at least one non-spherical optical element, and in some embodiments from at least two.

The focal state and magnification of the input OCT illumination changes systematically as a function of the scan angle along the major axis of the ellipsoidal elements. Various changes can be enumerated, each with its own impact on the image quality.

Firstly, the focus on the retina should be maintained. This should be considered because the signal drops rapidly as the spot size increases.

Secondly, the retinal signal (namely the illumination that is reflected back from the subject's retina and forms the basis of the image data), should be correctly coupled back to the OCT system. That is, collimation of the return signal must be maintained as incident onto the OCT fiber collimator so that the beam is accurately focussed onto the fiber and transmitted to the interferometer. The signal will drop rapidly if aberrations in the return beam are not compensated for prior to re-coupling the return light into the signal path.

Thirdly, the retina must be kept within the depth range of the OCT system. This applies to either OCT imaging in the spectral domain or swept source (time and coded frequency domain) OCT.

Fourthly, multiple reflecting surfaces (of the instrumentation and the retina of the patient under examination) and rapidly changing incidence angles which occur as a result of the scanning of the beams incurs a changing phase effect and/or altering polarization effect. This change in polarization/phase can destroy the interference between the sample and reference beams of the OCT system which is required in order to reproduce an image.

Fifthly, the overall system magnification will change as a function of scan field, which alters the corneal spot size and hence the retinal spot size and hence the resolution of the OCT system.

In addition, there is a trade off in implementation of the illumination system to provide the optimum transverse resolution of the retinal OCT. A larger spot size at the cornea will typically produce a smaller spot size in the retinal plane. However, in the context of widefield imaging through the described optical system, a larger beam diameter at the corneal plane will also mean a larger beam diameter at the plane of the scan transfer means, or ellipsoidal main mirror. Due the ellipsoidal geometry of the mirror, the beam shall incur greater aberration with increasing spot size. Correction of this aberration shall allow the benefit of a larger spot size, and hence increased spatial resolution, to be realised.

It is necessary to solve or at least partially solve one or more of these problems for any practicable application of an OCT system in integration with a wide field SLO system.

This present disclosure provides an aberration compensator, which ensures integrity of the OCT reference beam and sample beam as they propagate through a wide field SLO imaging system. The term aberration compensator is intended to encompass either a single element or a complex system of elements. Its functional elements may be located at one point along an optical path, or distributed at different points.

The aberration compensator may comprise a wavefront coding means for altering the wave front of the illumination source synchronously with the scanning.

This wave front coding means may be used to maintain focus (of the OCT beam) on the retina and to ensure that the retinal signal is correctly coupled back to the OCT system. The wave front coding means may be provided between the illumination source of the OCT optics 900 and the second scanning mirror.

According to one example embodiment, the wave front coding means may comprise a variable focus element provided with or at the illumination source to provide focal control of the illumination that the source emits.

This variable focus element may be a liquid lens which has its focal state controlled by selective application of an electromagnetic field, an adaptive lens which has its focal state controlled by the selective stroke of adaptive elements, or a variable position lens or lens system with its focal state controlled by relative positioning of lens elements. Lens adjustment mechanisms may be driven by suitable actuators such as piezoelectric actuators or other equivalents.

It is possible in alternative embodiments for a variable position lens system to comprise individual lens elements which may be one or the other of a liquid lens or an adaptive lens. Any possible combination of elements is included so long as the focus and magnification of the input beam can be varied synchronously with the scanning of the SLO/OCT apparatus.

Further, the wavefront coding means may also comprise an element for altering the input wavefront to compensate for focal control and higher order aberrations. This may be a spatial light modulator (SLM) or multi-element adaptive optics surface whereby the input beam is adjusted to compensate to aberrations from scan relay, synchronously with the scanning.

The aberrations from the scan relay are a function of the relay form, which are known. As such, the control of the wavefront coding means may be generated by a look up table containing the control parameters required for a given position in the frame scan.

Alternatively, the wavefront coding means may be controlled via a closed loop system whereby the wavefront is optimised to maximise fringe visibility or interferometric data signal.

The look up table of control parameters may be applied by a computer programme or embedded solution, such as a digital signal processor, and used to generate an angle dependent control signal for the aberration compensator. For example, this may be a voltage signal to drive a dynamic lens, a stepper motor signal to drive lens displacement or a multi-actuator signal to drive an adaptive correction solution.

Figure 7:
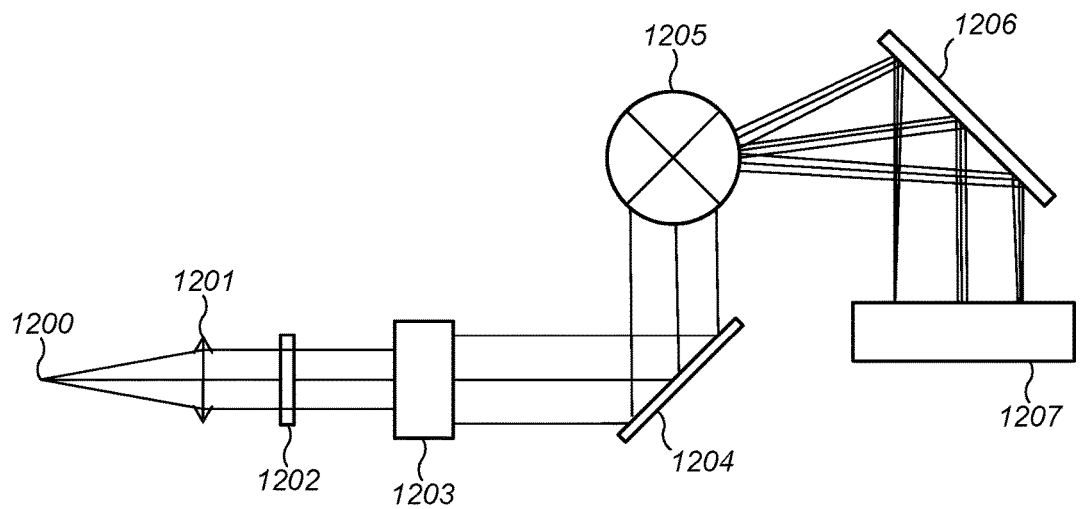
FIG. 7 illustrates an aspect of illumination control showing an adjustable lens used for aberration compensation.

FIG. 7 illustrates the operation of an embodiment of the disclosure, wherein a beam is introduced into system via fiber delivery 1200, and collimated at lens 1201. Element 1202 is a liquid lens component which controls the focal state of the beam introduced into scan system. Element 1203 is a magnification stage which may provide fixed or variable magnification of the input beam prior to a scan system.

The input beam is then directed to the scan system via mirror 1204 which may be a fixed mirror or may be an aberration compensator, such as a multi-element deformable mirror, a multi-segment actuated membrane mirror or a spatial light modulator. The beam is then passed onto a 2D scan system, 1205, and introduced to a widefield relay 1207 via element 1206, which may be a mirror or dichroic element.

The aberration compensation mechanism may in addition include a means for altering the optical path length of the OCT reference arm, in a manner synchronized with the scanning. This ensures signal integrity across the ultra wide field of the retina, as the varying optical path length means that the retina can be kept within the depth range of the OCT system.

The offset path length used may be dependent on the selected scan area in the ultra wide field image i.e. there may be a system related path length variance.

A means for automatically altering the path length during a scan to compensate for path length variance across the scan object (retina) may also be provided. This may be implemented by introducing a free-space optical path in the reference arm, where the path length of the free-space path is adjusted by use of a continuous or discrete motion stage. For example, the fiber reference arm may be fitted with a collimator to propagate a free space beam to a retro-reflector that returns the beam via the collimator to the reference fiber. Motion of either in the collimator or retro-reflector in the optical axis will introduce change in the overall path length of the reference arm.

The beam path length in the reference arm may be altered by rotation of a refractive prism set in the free space beam path, or alternatively by a series of adjustable mirrors forming a variable cavity within the open beam path. As a further alternative, the reference beam may be routed to a given beam path within a series of beam paths each of a discrete path length, providing a selectable reference arm length that is linked to the sample arm path length at a given scan location.

The path length in the reference arm must be matched to the path length in the retina, which alters over the scan time due to the curvature of the retinal object. The reference arm motion may be controlled by a look up table which implements a path length value according to the scan angle and, therefore, sample arm path length. The look up table may be fixed with values derived from a theoretical eye model, or may be variable according to a specific patient prescription.

The aberration compensation mechanism may in addition include a variable phase retardation stage.

In order to maximise fringe contrast and hence signal, it is important that the polarisation (or phase) of the light in the reference arm and object arm are matched at an interferometer of the OCT system. The phase effect of the optical scanning system and also the eye will have the effect of altering the object arm polarisation state as a function of scan angle.

For simplicity, it is preferable to implement the phase retardation stage on the reference arm to avoid intrusion of this mechanism in the input optical path of the object arm. However, this may be implemented on either the object or reference arm.

The variable phase retardation stage may comprise a waveplate or series of waveplates. Individual adjustment of this waveplates, by a rotary stage or motorised stage, for example, will introduce a known phase change to the beam propagating through the waveplates. This may be implemented in the free space beam as part of the optical path length control system.

Another embodiment of the variable phase retardation stage is a soleil-babinet type compensator, which comprises a birefringent wedge and a fixed wedge mounted onto a compensator plate which allows continuous variation of the phase retardation by adjustment of wedge elements relative to each other, such that the path length through the birefringent material is varied.

Another embodiment of the variable phase retardation stage is a stress-induced birefringence controller, whereby a variable mechanical stress on the fiber introduces a variable degree of birefringence and therefore phase retardation.

Figure 8:
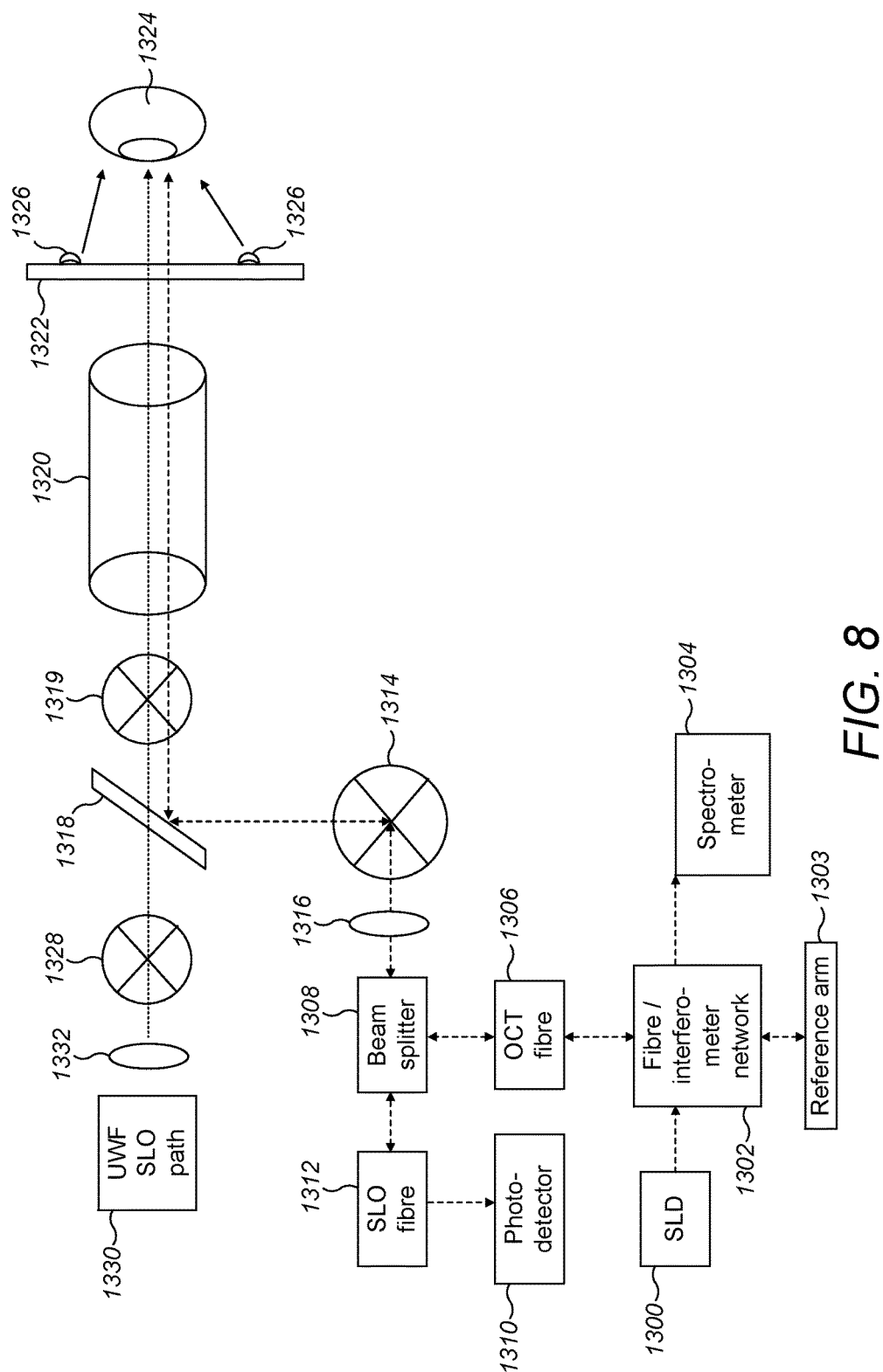
FIG. 8 illustrates an example of a suitable layout for an SLO optical system and OCT optical system as illustrated in FIGS. 4, 5, and 6.

FIG. 8 shows an example of a suitable layout for the SLO optical system 12 and the OCT optical system 900 as illustrated in FIGS. 4, 5 & 6. A light source 1300 such as a super luminescent diode (SLD) is directed to a fibre/interferometer network 1302 which provides an output to a reference arm 1303 (including the variable path length control and phase retardation stage), the object arm OCT fiber 1306 and the combined signal to a spectrometer 1304. The OCT fibre 1306 directs light to a local OCT scanner 1314, which may, for example be a MEMS scanner or a Galvanometer Scanner ("Galvo"), via the beam aberration control mechanism 1316, which may for example be a liquid lens, a spatial light modulator or an adaptive wavefront controller. The scanning element 1314 directs the illumination towards a hot mirror 1318 (IR-blocking mirror) and onwards through a scan relay 1320 via the second scanning element 1319 and towards the eye 1324.

Also shown is a patient alignment module, or PAM, 1322 which provides a patient fixation target via projection of an optical signal which may, for example, be visible LEDs 1326. In addition, an localised SLO may be derived using the return signal from the OCT illumination via beam splitter 1308, which directs the return illumination into a local SLO fiber 1312 and to a photodetector 1310, which can be used to generate a detailed SLO image in combination with the OCT acquisition. Finally the system of FIG. 8 comprises a first scanning element 1328 used by an ultra wide field SLO path 1330 with optical element 1332 which may for example be a lens.

It is to be appreciated that, with the systems described above, the OCT image itself may be a wide field image, which can extend up to the full extent of the wide field SLO image. It is also possible to acquire a targeted OCT image within the wide field retinal context. In both cases, the aberration compensator allows for the integration of the OCT system in the wide field context.

Modifications and improvements may be made to the above without departing from the spirit and scope of the present invention. For example, the magnifications of the elliptical relays may be adjusted to adjust the angular magnification to compensate for reduced mechanical scan angle of either scanner.

Also, although ellipsoidal coupling mirrors 18, 20 have been described and illustrated above, it should be appreciated that other coupling element may be used, such as diffractive elements, free form mirror surfaces or conventional lens relays, given the discrete wavelengths of the imaging system. Mirrors are better because of the reduction of chromatic effects from refractive coatings.

Also, the SLO 10 has been described and illustrated above as including scan relay device (slit mirror 18), it should be appreciated that this element is not essential and it is possible for the SLO 10 to provide the same advantages as described above without this component. Removing this component requires the laser beam to be "tilted" within the SLO, which causes some shearing effects on the images obtained. However, such an SLO is still capable of providing the two-dimensional scan from the apparent point source, regardless of its position relative to the larger area 62 (i.e. retina) and selected operating parameters.

Furthermore, although the first and second scanning elements 14 and 16 have been described and illustrated above as being a galvanometer mirror and a resonant scanner, respectively, it should be appreciated that other suitable scanning elements could be used, such as line scanning produced with a laser line source, or equivalent. Line scanning could be used as an effective alternative to point scanning. Here a line source produces a line illumination on the retina which is scanned orthogonally by a slow scanner. The line illumination is detected by a linear pixel array and a 2D image is built up by rotating the slow scanner.

Also, although the slit mirror 18 has been described above as being an ellipsoidal mirror having two foci, it should be appreciated that the scan relay device could take other forms. For example, the scan relay device could comprise an elliptical mirror, a pair of parabolic mirrors, a pair of paraboloidal mirrors or a combination of any of these components. The common technical feature provided by any of these component arrangements is that the scan relay device comprises two foci and produces a one-dimensional collimated light scan.

Where elliptical components are used in the scan relay device, it may also be necessary to provide beam compensation elements, such as cylindrical lenses.

Further, although the above described arrangement of the SLO 10 has the galvanometer mirror 14 positioned at the first focus of the slit mirror 18 and the resonant scanner 16 located at the second focus of the slit mirror 18, it should be appreciated that the position of the galvanometer mirror 14 and the resonant scanner 16 may be switched without affecting the operation of the SLO 10.

Furthermore, although the galvanometer mirror 14 has been described above as providing vertical scanning of the laser beam 13 and the resonant scanner 16 providing horizontal scanning, it should be appreciated that the axes of rotation and oscillation of these two elements could be switched, such that the galvanometer mirror 14 provides the horizontal scanning of the laser beam 13 and the resonant scanner 16 provides the vertical scanning. Therefore, the rotational axis of the second scanning element may be substantially parallel to the line joining the two foci of the scan transfer device and the line joining the two foci of the scan transfer device may lie substantially on the plane defined by the one-dimensional collimated light scan produced by the scan relay device; or the rotational axis of the second scanning element may be substantially perpendicular to the line joining the two foci of the scan transfer device and the line joining the two foci of the scan transfer device may be substantially perpendicular to the plane defined by the one-dimensional collimated light scan produced by the scan relay device.

In addition, although the above embodiment of the present invention has been described as providing 120 degree optical scans, it should be appreciated that the ophthalmoscope 10 may be configured to provide a lesser or greater angle of optical scan. As described above, this may be achieved, for example, by varying selection of the portion of the slit mirror 18 that the laser beam 13 is scanned across.

Also, the scan transfer device may comprise an elliptical mirror. The scan transfer device may comprise a pair of parabola mirrors. The scan transfer device may comprise a pair of paraboloidal mirrors.

Also, the rotational axis of the second scanning element may be within approximately 5 degrees of the line joining the two foci of the scan transfer device. The rotational axis of the second scanning element may be within approximately 2 degrees of the line joining the two foci of the scan transfer device. The rotational axis of the second scanning element and the line joining the two foci of the scan transfer device, may have a degree of parallelism which depends on chosen eccentricities of one or more components of the scanning ophthalmoscope. The rotational axis of the second scanning element and the line joining the two foci of the scan transfer device, may have a degree of parallelism determined by a user of the scanning ophthalmoscope, according to an acceptable level of shear in images of the retina produced by the ophthalmoscope.

Also, the rotational axis of the first scanning element may be within approximately 5 degrees of the line joining the two foci of the scan transfer device. The rotational axis of the first scanning element may be within approximately 2 degrees of the line joining the two foci of the scan transfer device. The rotational axis of the first scanning element and the line joining the two foci of the scan transfer device, may have a degree of parallelism which depends on chosen eccentricities of one or more components of the scanning ophthalmoscope. The rotational axis of the first scanning element and the line joining the two foci of the scan transfer device, may have a degree of parallelism determined by a user of the scanning ophthalmoscope, according to an acceptable level of shear in images of the retina produced by the ophthalmoscope.

Furthermore, the line joining the two foci of the scan transfer device may be within approximately 5 degrees of the plane defined by the one-dimensional collimated light scan produced by the scan relay device. The line joining the two foci of the scan transfer device may be within approximately 2 degrees of the plane defined by the one-dimensional collimated light scan produced by the scan relay device. The line joining the two foci of the scan transfer device and the plane defined by the one-dimensional collimated light scan produced by the scan relay device, may have a degree of coincidence which depends on chosen eccentricities of one or more components of the scanning ophthalmoscope. The line joining the two foci of the scan transfer device and the plane defined by the one-dimensional collimated light scan produced by the scan relay device, may have a degree of coincidence determined by a user of the scanning ophthalmoscope, according to an acceptable level of shear in images of the retina produced by the ophthalmoscope.

Also, although not illustrated above, in an optional step of FIG. 5 the retina can be scanned in an axial manner to produce a three-dimensional image.

Furthermore, although the first and second scanning elements have been described and illustrated above as oscillating mirrors, it should be appreciated that the first and second scanning elements may comprise line scanning elements. The line scanning element may comprise a laser line scanner. The laser line may be generated by a diffractive optical element, cylindrical lens, or other known means of creating a laser line.

Also, although the scanning elements have been described above as having operating parameters which allow the direction of the two-dimensional collimated light scan from the apparent point source can be controlled, it should be appreciated that if the scanning elements are line scanning elements (e.g. laser line scanner), the operating parameters are operable to adjust the dimensions (i.e. horizontal/vertical) of the two-dimensional collimated light scan from the apparent point source. This allows the size and position of the scan area to be adjusted, and hence effectively "moved" around the retina to obtain a montage of images thereof. Where line scanning elements are used, it is important to note that the detection and AO layout architecture is also modified, as is known in the art.

The invention claimed is:
1. A scanning ophthalmoscope for scanning the retina of an eye, the scanning ophthalmoscope comprising:

a source of collimated light and a scanning device which together provide a two-dimensional collimated light scan from an apparent point source;

a scan transfer device comprising a first focus at which the apparent point source is provided and a second focus at which an eye may be accommodated, and wherein the scan transfer device transfers the two-dimensional collimated light scan from the apparent point source into the eye;

an optical coherence tomography (OCT) system comprising a radiation source and an optical system that together provide OCT reference and sample beams where the sample beam propagates along at least part of the same optical path of the light emitted by the source of collimated light and propagating through the scan transfer device, and an aberration compensator that automatically compensates for systematic aberrations and/or changes in wavefront introduced by the scan elements and scan transfer device as a function of scan angle.

2. The scanning ophthalmoscope as claimed in claim 1, wherein the aberration compensator is configured to alter the wavefront of the illumination emitted by the OCT illumination source, to compensate for aberrations and changes in wavefront introduced by the scan elements and scan transfer device as a function of scan angle.

3. The scanning ophthalmoscope as claimed in claim 2, wherein the aberration compensator comprises a device for altering the spatial properties of the incident beam and/or the form of the incident beam wavefront such that the spatial extent of the input OCT signal on a retinal surface is minimised after propagation through the scan transfer device.

4. The scanning ophthalmoscope as claimed in claim 2, wherein the aberration compensator comprises a variable magnification stage to optimise the beam diameter at any point in the scan field.

5. The scanning ophthalmoscope as claimed in claim 2, wherein the aberration compensator comprises a variable focus element.

6. The scanning ophthalmoscope as claimed in claim 5, wherein the aberration compensator comprises at least one of a liquid lens, an adaptive lens, a spatial light modulator, a variable position lens or lens system, or an adaptive optical system.

7. The scanning ophthalmoscope as claimed in claim 1, wherein the aberration compensator is configured to alter the optical path length of the OCT reference arm, such that the sample and reference path lengths remain matched throughout said scanning.

8. The scanning ophthalmoscope as claimed in claim 7, wherein the aberration compensator comprises a motorised linear translation stage whereby the optical path length may be increased or decreased to match the sample arm path length throughout said scanning.

9. The scanning ophthalmoscope as claimed in claim 8, wherein the aberration compensator comprises a series of rotating optical elements to provide adjustable path length control such that the optical path length may be increased or decreased to match the sample arm path length throughout said scanning.

10. The scanning ophthalmoscope as claimed in claim 7, wherein the aberration compensator comprises a series of fixed paths of varying path length that may be selectively enabled to match the input sample path length.

11. The scanning ophthalmoscope as claimed in claim 7, wherein the aberration compensator comprises a feedback mechanism so that the path length can be automatically altered during a scan to compensate for path length variance during a scan.

12. The scanning ophthalmoscope as claimed in claim 7, wherein the aberration compensator comprises means for automatically altering the path length in discrete steps between each sample during a scan.

13. The scanning ophthalmoscope as claimed in claim 1, wherein the aberration compensator comprises a variable phase retardation stage such that the polarisation state of the signal and reference beams remains matched throughout said scanning.

14. The scanning ophthalmoscope as claimed in claim 13, wherein the phase retardation stage is provided in the OCT reference arm.

15. The scanning ophthalmoscope as claimed in claim 13, wherein the phase retardation stage comprises one of: a waveplate; a series of waveplates; a soleil-babinet type compensator; a stress-induced birefringence controller.

16. The scanning ophthalmoscope as claimed in claim 1, wherein the scan transfer device comprises an ellipsoidal mirror.

17. The scanning ophthalmoscope as claimed in claim 1, further comprising a light detection device for detecting light reflected from the retina to produce an image of the scanned area of the retina.

18. The scanning ophthalmoscope as claimed in claim 1, wherein the scanning device comprises a first scanning element and a second scanning element.

19. The scanning ophthalmoscope as claimed in claim 18, wherein a rotational axis of the second scanning element is substantially parallel or perpendicular to a line joining the two foci of the scan transfer device.

20. The scanning ophthalmoscope as claimed in claim 18, wherein the rotational axis of the first scanning element is substantially parallel or perpendicular to a line joining the two foci of the scan transfer device.

21. The scanning ophthalmoscope as claimed in claim 18, wherein the OCT radiation source is provided at a position along the optical path before the first scanning element.

22. The scanning ophthalmoscope as claimed in claim 18, wherein the OCT radiation source is provided at a position along the optical path after the first scanning element and before the second scanning element.

23. The scanning ophthalmoscope as claimed in claim 1, wherein the OCT radiation source is provided via a separate input path and directed to a retina via the scan transfer means at an arbitrary angle relative to the SLO beam.

24. A method of scanning the retina of an eye, the method comprising the steps of:

providing a source of collimated light and a scanning device which together provide a two-dimensional collimated light scan from an apparent point source;

providing a scan transfer device comprising a first focus at which the apparent point source is provided and a second focus at which an eye may be accommodated, and wherein the scan transfer device transfers the two-dimensional collimated light scan from the apparent point source into the eye;

providing an optical coherence tomography (OCT) system comprising a radiation source and an optical system that together provide OCT reference and sample beams where the sample beam propagates along at least part of the same optical path of the light emitted by the source of collimated light and propagating through the scan transfer device; and compensating for systematic aberrations and/or changes in wavefront introduced by the scan elements and scan transfer device as a function of scan angle.

25. The method of claim 24, wherein the step of compensating for aberrations comprises altering the wavefront of the illumination emitted by the OCT illumination source, to compensate for aberrations and changes in magnification introduced by the scan elements and scan transfer device as a function of scan angle.

26. The method of claim 24, wherein the step of compensating for aberrations comprises altering the optical path length of the OCT reference arm, such that the sample and reference path lengths remain matched over the full extent of a retinal scan.

27. The method of claim 24, wherein the step of compensating for aberrations comprises controlling the phase of OCT illumination such that the polarisation state of the signal and reference beams remains matched over the full extent of a scan.

28. A scanning ophthalmoscope for scanning an eye, the scanning ophthalmoscope comprising:
an optical system that is configured to provide a reference beam and a sample beam for optical coherence tomography;
a scanning device which, together with the sample beam, is configured to provide a light scan from an apparent point source; and
a scan transfer device comprising a first focus at which the apparent point source is provided and a second focus at which an eye is accommodated to transfer the light scan from the apparent point source into the eye.

29. The scanning ophthalmoscope as claimed in claim 28, further comprising
an aberration compensator that is configured to compensate for at least one of an aberration and change in wavefront of the sample beam introduced by at least one of the scanning device and the scan transfer device as a function of scan angle.

30. The scanning ophthalmoscope as claimed in claim 29, wherein the aberration compensator is configured to alter the optical path length of the reference beam to be matched with the optical path length of the sample beam.

31. The scanning ophthalmoscope as claimed in claim 30, wherein the aberration compensator comprises a series of rotating optical elements to provide optical path length control.

32. The scanning ophthalmoscope as claimed in claim 28, wherein the scan transfer device comprises an ellipsoidal mirror with two foci, wherein one focus of the ellipsoidal mirror is the first focus at which the apparent point source is provided, and the other focus of the ellipsoidal mirror is the second focus at which the eye is accommodated.

33. The scanning ophthalmoscope as claimed in claim 29, wherein the aberration compensator comprises a variable phase retardation stage that is configured to match a polarization state of the sample beam reflected from the eye with the polarization state of the reference beam.

34. The scanning ophthalmoscope as claimed in claim 28, further comprising a second optical system for a scanning laser ophthalmoscope, wherein the sample beam is arranged to propagate along at least part of the optical path of the second optical system.

* * * * *